United States Patent [19]

Longstaff

[11] Patent Number: 4,793,668
[45] Date of Patent: Dec. 27, 1988

[54] SUNBATHING FILTER WITH INCOMPLETE UV-B ABSORPTION

[76] Inventor: Eric Longstaff, 5 Cantey Pl., Atlanta, Ga. 30327

[21] Appl. No.: 930,602

[22] Filed: Nov. 13, 1986

[51] Int. Cl.[4] ............................ G02B 5/22; G02B 7/00
[52] U.S. Cl. ..................................... 350/1.1; 350/311; 350/318
[58] Field of Search .......................... 350/1.1, 311, 318

[56] References Cited

U.S. PATENT DOCUMENTS

| | | | |
|---|---|---|---|
| 2,391,959 | 1/1946 | Gallowhur | 2/78 |
| 3,352,058 | 11/1967 | Brant | 47/58 |
| 4,134,875 | 1/1979 | Tapia | 260/42.66 |
| 4,179,547 | 12/1979 | Allingham et al. | 525/2 |
| 4,200,360 | 4/1980 | Mutzhas | 350/316 |
| 4,529,269 | 7/1985 | Mutzhas | 350/312 |

FOREIGN PATENT DOCUMENTS

| | | |
|---|---|---|
| 930621 | 8/1947 | France . |
| 1540568 | 2/1979 | United Kingdom . |
| 1586687 | 3/1981 | United Kingdom . |
| 2097810 | 11/1982 | United Kingdom . |

OTHER PUBLICATIONS

Potten, C. S., "Radiation and Skin", (1985), p. 192.
Hönigsmann, M.D., H. et al, "Immediate Pigment Darkening Phenomenon, A Reevaluation of its Mechanisms", (1986).
Black, G. et al, "Lack of Photoprotection against UV-B-Induced Erythema by Immediate Pigmentation Induced by 382 nm Radiation", (1985).
Gange, R. W. et al, "Comparative Protection Efficiency of UVA- and UVB-Induced Tans . . . Sensitive Sites in DNA by UVB in Human Skin", (1985).
Arase & Jung, "How We Do It—In Vitro Evaluation of the Photoprotective Efficiency of Sunscreens Against DNA Damage by UVB", (1985).
U.S. Dept. of H.E.W., NIOSH—"A Recommended Standard for Occupational Exposure to Ultra Violet Radiation", (1977).
Strickland, P. T., "Photocarcinogenesis by Near-Ultraviolet (UVA) Radiation in Sencar Mice", (1986).
Kugman & Kugman, "Review Article—The Nature of Photoaging: Its Prevention and Repair", (1986).

Primary Examiner—Bruce Y. Arnold
Attorney, Agent, or Firm—Louis T. Isaf

[57] ABSTRACT

Apparatus for use in sunbathing comprises a screen formed of a sheet of thermoplastic or fiber material which is transparent to the safe UV-A wavelengths of solar radiation and the visible light range between 400–450 nm but which contains uniformly distributed therethrough a first agent which absorbs at least 80% of the UV-B radiation in the 310—320 nm range and all radiation below 310 nm, and a second agent and third agent which prevent transmission therethrough of some radiations above 450 nm wavelength, i.e. visible light and infra-red. The second agent may be an absorbing dye or pigment. The third agent may be finely divided carbon or ground glass. The screen may be mounted on a frame or fabricated into clothing so as to shield the sunbather from the acutely and chronically harmful wavelengths of radiation, to prevent unpleasant overheating, and to provide subdued lighting. The relatively small amount of UV-B transmitted through the material stimulates the production of new melanin in a sunbather, and this melanin will be later available for tanning by UV-A radiation.

11 Claims, 2 Drawing Sheets

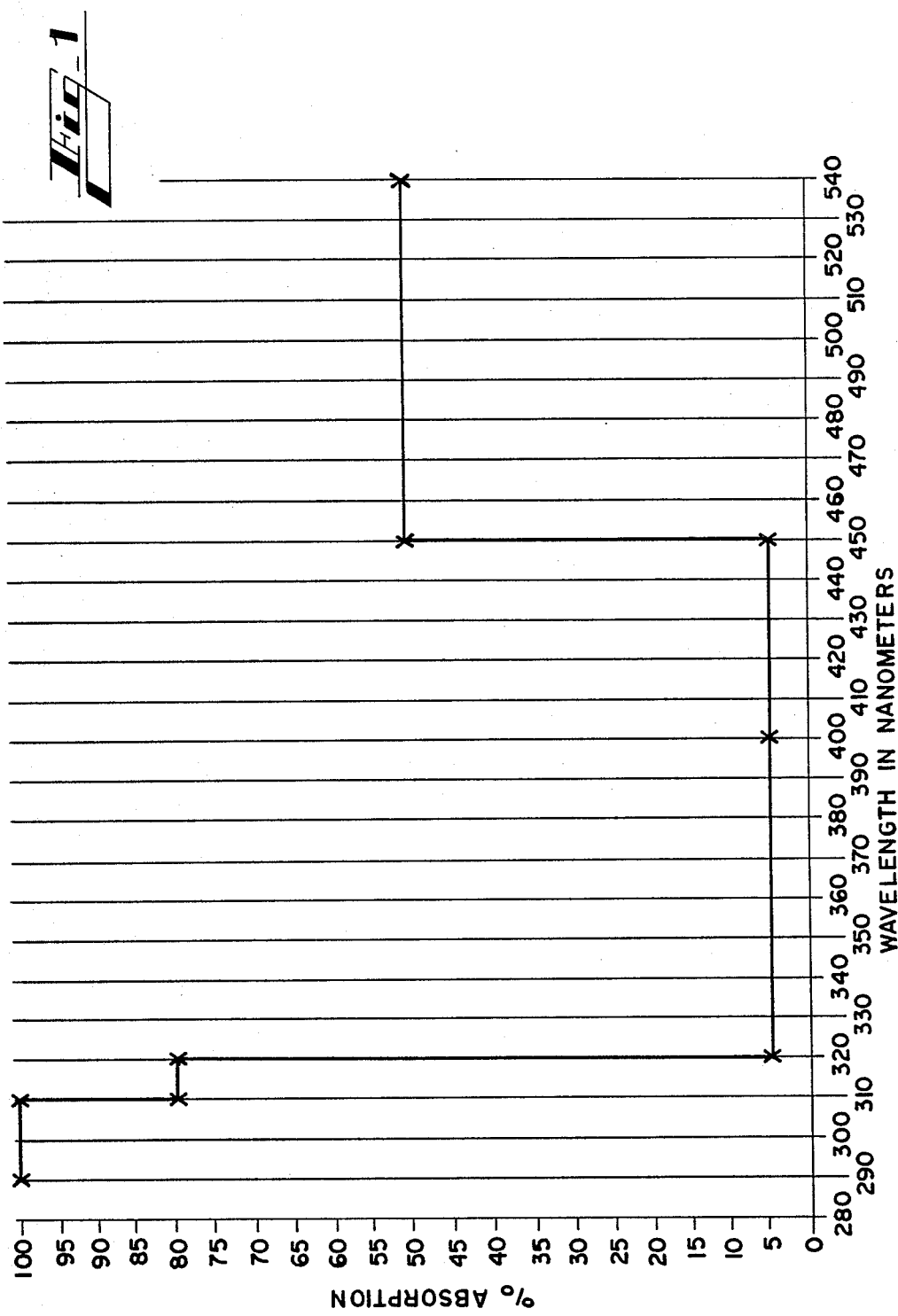

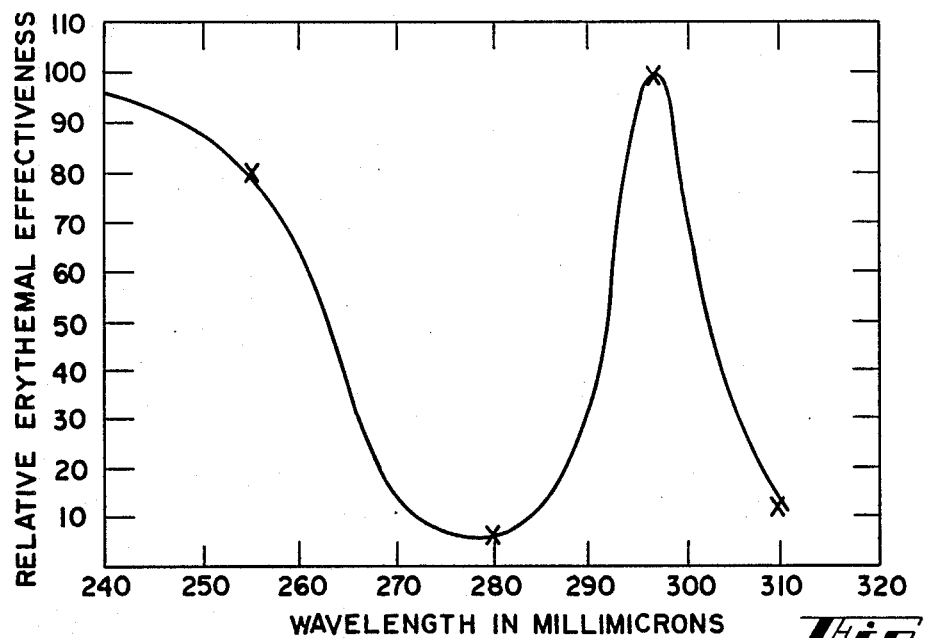
Fig_2
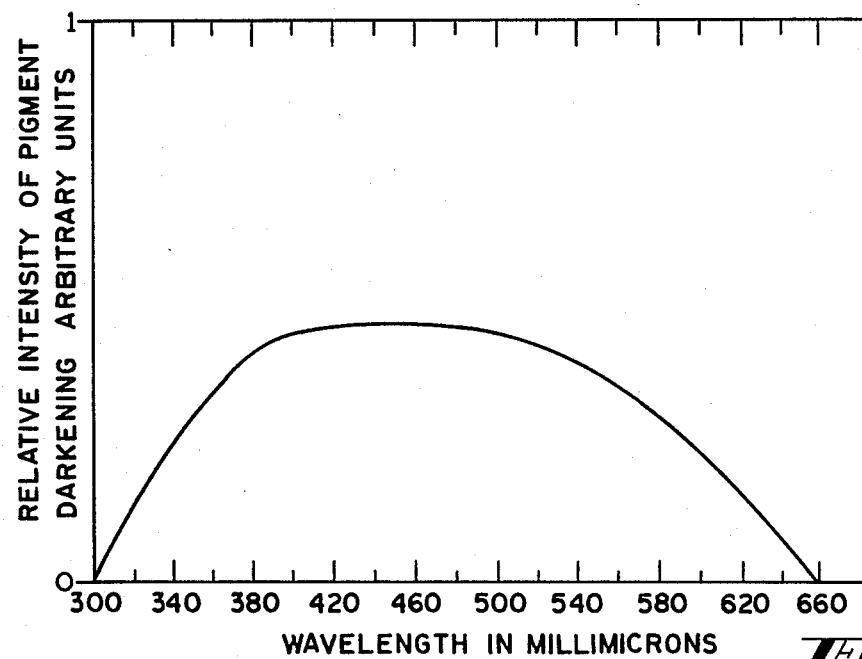
Fig_3

SUNBATHING FILTER WITH INCOMPLETE UV-B ABSORPTION

FIELD OF THE INVENTION

This invention relates in general to the definition of fabrics for use in the construction of filters suitable for protecting human skin from the damaging effects of excessive exposure to solar radiation while permiting immediate pigment tanning and encouraging de novo melanin synthesis. In addition, persons sunbathing in the shadow cast by the embodiment of this invention will be protected from the damaging effects of excessive heat, eye-strain and sunburn, but will nevertheless enjoy the benefit of a cosmetically appealing tan which will progressively protect them from solarization-induced erythema, skin-aging, and possible malignant and other chronic disorders.

BACKGROUND OF THE INVENTION

Many varied attempts have been made previously to formulate and construct a safe sun-screen which would encourage protective suntanning but these have been generally ineffective because they are specifically designed to remove all, or substantially all of the entire short wave UV-B (290–320 nm) either by employing chemical absorbers (e.g. Gallowhur U.S. Pat. No. 2,391,959; Solvay et Cie, French Pat. No. 2,236,195, Sear U.K. Pat. No. 2,097,810, Mutzhas U.S. Pat. No. 4,529,269), by mechanical processing of thermoplastic resins or yarns so as to impart UV-B filtering characteristics (e.g. Solvay et Cie, French Pat. No. 7,324,647; Stotzer, French Pat. No. 8,020,161; Mariac, French Pat. No. 930,621; Glaser, West German Pat. No. 3,101,390) or by including ground glass particles in the support resin and providing multiple spatially arranged laminates each with unique but additive absorption characteristics (e.g. Mutzhas, British Pat. Nos. 1,586,687 and 1,567,979 and U.S. Pat. No. 4,200,360).

However, no previous attempts have been made to preferentially reduce only certain wavelengths in all three categories of dangerous light, which it now seems can interact synergistically to represent a very serious cosmetic and health threatening environment to man, while at the same time providing sufficient transmission of certain wavelengths of UV-B energy within the narrow band 310–320 nm now known to stimulate melanogenesis.

Recognition of the health hazard of UV-radiation has already prompted the U.S. Department of Health Education and Welfare (via NIOSH) to recommend occupational exposure limits to UV radiation including that of natural sunlight (HSM Pub. Nr. 73-11009) and there have also been calls by general medical practitioners for stricter controls on UV-parlors. Also, a recent U.S. Bureau of Food and Drug Administration advisory panel recommended after reviewing available topical sunscreens, that all sun protection products should be placarded with the advisory phrase "Over-exposure to the sun may lead to premature aging of the skin and skin cancer. The liberal and regular use of this product may reduce the chance of premature aging of the skin and skin cancer".

In addition, safety plastic or glass filters have been formulated and used for eye protection against the very short wavelengths ultra-violet rays (UV-C) artificially produced by electric carbon arc welding equipment. These glasses employ very broad spectrum UV blockers such as acetophenone and pigments or dyes such as the soluble green dyestuff "Filter Blaugrun" as visible light filters (British Pat. No. 1,060,780). Such materials are totally unsuitable for sunbathing because they entirely block the harmless UV-A light necessary for immediate pigment darkening as well as the small proportion of UV-B within the wavelength range 310–320 nm which is essential for melanogenesis.

It can be seen therefore that the disadvantages of these earlier radiation screens are that they are either prohobitively expensive to produce, overprotect the sunbather from the UV-B sunburning and melanogenic rays, do not protect from the overheating infra-red rays or they block out all the UV-light and prevent tanning altogether. None of the prior art inventions relating to applied sunscreens are able to protect the sunbather from dangerous intense visible or infra-red light which is now thought to be potentially as dangerous as excessive short wave band (290–310 nm) UV-B with respect to cancer induction and skin aging, nor do they provide for a mechanism whereby de novo melanin synthesis can be encouraged.

SUMMARY OF THE INVENTION

The basic object of the current invention is therefore a non-applied radiation-protective filter which makes it possible in the case of natural solar or artificially generated solar radiation to simultaneously tan quickly by inducing the immediate pigmend darkening of pre-existing cutaneous melanin and to also initiate new pigment synthesis at a greater rate in a pleasant and safe manner.

This object is accomplished according to the invention by interposing a filter made of solid material between the sun and the body which blocks out radiation energy intensities in those wavelength ranges which are physiologically harmful but not to completely inhibit a mild painless erythema which is the stimulus for de novo pigment synthesis.

In order to understand full the significance of these improvements in the design and construction of sun-selecting filters and fabrics, it is first necessary to reveiw in detail the natural process of suntanning. Terrestrial sunlight has been considered to consist of, with very slight variations of definintions, short-wave ultra-violet light (UV-B, 290–320 nm), long-wave ultraviolet light (UV-A, 320–400 nm), visible light (400–700 nm) and infra-red light (wavelengths ranging from 700 nm to 15 microns). On a clear day at sea level, the distribution of solar radiation is about 1–2% UV, 42–53% visible light and 57–63% infra-red. At higher altitudes at any given latitude, the amount of solar radiation avaiable, especially UV, is increased so much that at the highest altitudes at sub-zero temperatures a climber needs very effective sunburn protection.

Generally, it is now recognized that all UV-B is dangerous to health and excessive natural exposure can lead to sun-burn (erythema), skin aging and cancer. However, not all wavelengths of UV-B are equally dangerous, the range 310–320 nm being at least so. UV-A is apparently harmless at natural intensities and induces immediate pigment darkening or skin tanning. Visible or white-light has also been considered safe although there are now reports that there are some disorders of the skin, particularly those involving photosensitivity reactions, skin aging and cancers, which can occur in those individuals exposed to intense light. The most serious commonly occurring hazards of excessive exposure to visible and infra-red light involve dehydration due to over-heating, ultimately leading to unconsciousness, sunstroke and even death.

Current literature surveys confirm that the deleterious rays of the sun are in the UV region and the sunburning rays (UV-B) are carcinogenic. UV-A on the other hand requires vastly higher exposure doses that UV-B to produce papillomas and carcinomas.

Sunlight extend from the UV-region into the regions of visible light, infra-red and ultimately radio waves. The latter can probably be disregarded with respect to dermal effects, but visible radiation cannot. Harmful effects such as phototoxic reactions through DNA cross-linking to tumor enhancement have been recorded. Visible light also causes solar urticaria in some people.

The precancers and cancers resulting from excessive and prolonged UV radiation are now well recognized, but the fact that acute heat exposure can also cause squanmous cell carcinomas or that chronic heat exposure in the physiological range can result in neoplasms induction is insufficiently well appreciated. Evidence for these effects is derived from China (Kang cancers), India (Kangri cancers of Kashmir), Japan (Kairo cancer), Ireland (Turf or Peat Fire Cancer), and Australia (epithelioma due to spectacles focusing IR radiation on the cheeks. The similarities between IR and UV induced skin cancers are strikingly obvious. In addition, it seems that skin aging (Elastosis and the like), erythema ab igne, and cancers, can be produced by either route and indeed there is a distinct probability that enhancement of chronic actinic damage by IR radiation is of great importance in the etology of human cancers. Clearly, whenever insulation is high, heat is a concomitant factor and sunbathing in the midday sun entails being irradiated by the far from innocuous UV-B and IR rays.

It is advocated in the prior art that to protect the skin of the human body against sunburn which is generated by excessive exposure to wavelengths of sunlight shorter than 320 nm (UV-B), it is helpful to either coat the body with suntan oil, cream or lotion, or to protect the skin by remaining in the shade of an absolute UV-B filter. The suntan cosmetics function by including in their formulation a histocompatible UV-B filter, the concentration and specificity of which defines the sun protection factor (SPF) afforded by the product.

In a similar manner, physical sunscreens such as polyvinyl chloride resins in the form of films have been described which contain UV-B blocking agents which remove substantially all the available energy in the wavelengths shorter than 320 nm, and thus have an infinite sun protection factro which totally inhibits erythema. Both these types of products have inherent weaknesses in their design. In the former case of suntan lotions and related cosmetic preparations, one cannot assume with certainty that every part of the exposed part of the body is adequately covered and protected, and indeed the protective liquid film may be inadvertently removed by rubbing against a towel or during swimming. Further, no protection against eyestrain or overheating is provided even by the most carefully applied cosmetic system and it has even been suggested that some of the chemical ingredients in suntan lotion preparations may be in themselves chemical carcinogens, mutagens or photoallegens. In the latter case of physical barriers to UV-B, those which have been described to date are constructed so as to remove all UV-B radition while permitting some UV-A transmission for immediate pigment darkening effects. It is now known that UV-A at natural intensities will not initiate melanogenesis to any significant degree and that the tan effect induced by UV-A will not protect from sunburning by UV-B. Thus, while such physical instruments are not dangerous in themselves they do not promote the essential de novo synthesis of new pigment which is required if the sunbather intends to pursue the habit of suntanning over several days or weeks and gain not only an immediate light tan but a self-protecting deep suntan derived from the darkening of greater quantities of recently synthesized melanin pigment.

To get a good lasting and protective tan according to the present invention, a small daily dose of UV-B radiation is needed to stimulate the malanocytes to produce greater quantities of new melanin which will be later available for tanning by the UV-A. This essential further synthesis of melanin starts between 2 and 19 days after the first exposure, especially to those wavebands which acutely damage the epidermis (i.e., 290-320 nm), but sufficient stimulation has been shown to be achieved with the present invention within the restricted wave band 310-320 nm without a painful erythemic response resulting.

The objective of the current invention is therefore realized by careful formulation so as to provide an apparatus for the transmission of experimentally predetermined maximum energy levels characterized in terms of milliwatts per square centimeter of exposed skin at given wavelengths or ranges. Also, because the apparatus may need to be used for protracted periods for sunbathing in areas of high solarization, the effective and useful life of the material needs to be carefully extended and defined by the incorporation of free-radical scavengers and other substances known to be suitable by those skilled in the art of extending the weatherability of exposed synthetic fabrics.

Embodiments of the invention will now be further described with references to the accompanying drawings.

BRIEF DESCRIPTION OF DRAWINGS

FIG. 1 is an absorption diagram illustrating ideal absorption characteristics within the wavelength range 290-540 nm for a sunscreen apparatus according to a preferred embodiment of the present invention.

FIG. 2 illustrates the relative erythemic effects of UV energy produced by various wavelengths that is, the relative effectiveness of ultraviolet energy of various wavelengths in producing erythema. [Taken from M. A. Pathak, F. C. Riley and T. B. Fitzpatrick, Journal of Investigative Dermatology 39, p. 435 (1962).]

FIG. 3 illustrates the action spectrum for immediate pigment darkening. [Taken from M. Luckiesh and A. H. Taylor, General Electric Review 42, p. 274 (1939).]

DESCRIPTION OF PREFERRED EMBODIMENTS

The plastics material, which preferable is a thermoplastic material or acrylic resin in the form of either a thin film or woven or knitted material, must exhibit the property of being transparent to long wave UV-A radiation of wavelengths between 320 and 400 nm and to visible light in the range between 400 and 450 nm which are those particularly associated with immediate pigment tanning. In addition, the intense light associated with eye damage within the range 450-700 nm and a major portion of the IR wavelengths greater than 700 nm are absorbed to exclude the heating element of the sun's radiation, prevent carcinogenesis, and teh synergistic effects which cause skin aging or tumor promotion.

Suitable materials for the screen support material, when in film form, are resins of vinyl chloride, polyolefins such as polyethylene and polypropylene, or acrylic resins such as polymethyl-methacrylate. The vinyl chloride resins referred to are homopolymers or copolymers of vinyl chloride and such resins may, in addition, contain plasticizer preferably of phathallate esters. Copolymers such as polyethylene/vinyl acetate and butadiene/styrene would also suffice.

A preferred material for the screen is a plasticized polyvinyl chloride film of thickness between 100 and 300 microns, for example, 175 microns, and this may be a single film or a laminate formed with a reinforcing nylon or polyester net to give greater physical strength.

Whichever of the aforementioned resins is used, it should not have a significant absorption, i.e., greater than 30%, of radiation of wavelengths between 310 and 450 nm. The resin should also be light-stable and nonvolatile at the relatively high temperatures used in extrusion or callendering (i.e. about 150°–200° C.). Because these resins are transparent to substantially all of the available energy into the UV-A and UV-B wavelengths and most of the visible and IR spectrum, additional agents described below need to be added to the formulations to selectively filter the wave bands of light previously mentioned in order to achieve the desired photobiological effects.

As an alternative to rigid or plasticized thermoplastic film, a woven or knitted fabric perferably of nylon or polyester filaments may be employed as the support material. The advantage of this form of the invention is that such fabrics may readily be made up into wearing apparel. A suitable support material is the polyester polyethylene terephthalate. Care must be taken to ensure that the particular cross-section of fiber, the number of fibers per element and the orientation of the fiber in the woven or knitted fabric does not cause excessive light reflection or defraction. Suitable examples include first, ICI polyester 15 50 desitecs weight, 20 filament round cross-section T1001 Terinda ® yarn made up by Tricot warp knitting as a fabric having a locknit within the range 21–40 kneedles per inch, for example 28 gauge knitting. The fabric weight should be less than 100 gm/meter$^3$, for example 86 gm$^3$ at 16 wales/cm×21 courses/cm.

A second fabric alternative to rigid film would be Tietex ® 18 gauge warp-knitted polyester. This particular fabric has highly organized linear orientated fibers which minimizes light defraction and encourages high general light transmission.

Because these polyesters have a high UV-B absorbing capacity in their own right, i.e. without additional UV absorbing agents, only those agents imparting visible and IR absorption need be added to create an ideal sunscreen according to the invention.

The agent used typically in the rigid or plasticized film to achieve UV-B leakage in the range 310–320 nm is ethylhexyl-p-methoxycinnamate at a concentration of 0.05% w/w, when the film thickness is between 100–300 microns. (As used throughout this specification, "w/w" refers to "weight for weight".) For the same film, pigments such as Microlith Violet B-K, Cromoptal Blue A3R (Ciba-Geigy) and PV Carmine HF4C (Hoescht) at a concentration of 0.1% w/w provide ideal visible light absorption as well as imparting attractive coloration, and a heat sink comprising thermal black (finely divided carbon black) at a concentration of for example, 0.5% w/w to absorb IR radiation. Film compounded from plasticized PVC and containing the above ingredients serves to transmit 20% UV-B in the wavelength range 310–320 nm, but excludes substantially all UV-B in the range 290–310 nm. This transmitted quantity of UV-B energy represents a maximum skin surface UV-B radiance of about 1 mW/cm$^2$.

Similar levels of UV-B irradiance in the range 310–320 nm would be achieved by deployment of the previously described fiber fabrics, suitably surface printed or dyed with disperse dyes such as Dispersol Red B2-B at 2.25% w/w concentration. Infra-red may be absorbed by carbon black as previously described or reflected by titanium dioxide. The selection of suitable pigments and dyestuffs is of course important in the invention from two standpoints. Firstly, the colors must not absorb UV light between 320 and 400 nm or between 400 and 450 nm; otherwise the efficiency of the sunscreen will be impaired; and secondly, they must be light fast. The integrity of the finished sunscreen according to the invention maintained after 400 hours QUV when exposed to artifical accelerated weathering according to ASTM G53-77. (QUV, as used herein, refers to "Quartz UV Light", which defines a known process of accelerated weathering using artificial light.)

The apparatus may comprise a framework adapted to support said sheet or fabric material. Such framework may comprise a central support member and a plurality of support rods extending radially from one end of said central support member. Preferably, the support rods are hingedly attached to the central support member whereby the apparatus may be folded for storage and/or transportation purposes.

Alternatively, the support rods may be detachably securable to the central support member for such purposes.

Alternatively, the framework may comprise a plurality of support rods over which said sheet material may extend so as to define a screened space therebelow. In this case, the support rods may be hingedly or detachably secured to each other.

As a further alternative the sheet material may be adapted to be worn by a person so as to shield a part of that person's body, for example in the form of a hat.

Referring now to FIG. 1, there is shown a spectrograph idealizing the absorption characteristics of the present invention. Very little of the shorter range UV-B (in the wavelength range 290–310 nm) is transmitted while about 20% of the available longer-range UV-B in the wavelength range 310–320 nm is transmitted, which represents a maximum possibly achievable global energy level of about 1 mW/cm$^2$ at the exposed skin surface.

Referring now to FIG. 2, it can be seen that from recent estimates of the erythema action spectrum which have shown that the effectiveness of UVR at wavelengths greater than 300 nm drops off very rapidly, falling at 320 nm to about 1% of that at 300 nm (Farr & Diffey 1985), the present invention permits minimal erythema within those wavelengths ranges now known to initiate new melanin synthesis.

Referring now to FIG. 3, it can be seen that immediate pigment darkening (darkening of already existing melanin, probably as a result of an oxidation reaction) is caused by a broad band of radiation extending from 300 nm to 660 nm, with a maximum effect occurring between 360 and 440 nm. By comparison of these data with the spectral characteristic of the present invention described in FIG. 1, it can be realized that adequate transmission of these wavelengths needed for melanin darkening are transmitted by the present sunscreen material.

It should now be seen how the prior art is extended by the current invention to accommodate new concepts of the mechanism of suntanning and the knowledge that the protective value of a suntan gained after several days exposure to wavelengths in the UV-B range about 310 nm is more protective against further UV-B insult than that generated by only UV-A.

In the many possible embodiments of the apparatus of the invention the sheet material is transparent to the tanning UV-A radiation, but includes substances which absorb all of the UV-B radiation in the 290 to 310 nm wavelength range, all but 20% in the range 310–320 nm, as little as possible in the range 320–450 nm, and at least 50% of the visible light and IR wavelengths above 450 nm. By means of the invention a person can be shielded from the deleterious effects of the sun and will develop a tissue protective suntan while relaxing or being active outdoors without the necessity of either the frequent application of creams, lotions or the like or the wearing of restricting or undesirable clothing.

Alternative embodiments of apparatus will be readily apparent to persons skilled in the art. For example the screen material may be laminated with nylon or polyester net to provide sufficient strength for it to be used for example, as a roof for an enclosure such as a swimming pool or tennis court. Also many other configurations of framework may be used, for example, a simple upright support screen. Alternatively the screen material may be formed in the shape of, for example, a wide brimmed hat such as may be worn by a person exposed to the sun.

It should be understood that the foregoing relates only to preferred embodiments of the present invention, and that many changes and modifications can be made therein without departing from the spirit and scope of the invention as defined in the following claims.

I claim:

1. Apparatus for use in sunbathing, comprising:
 a substrate screen material which is substantially transparent to the safe UV-A wavelengths of solar radiation in the range 320–400 nm and light in the range 400–450 nm;
 which said substrate containing at least one first agent which absorbs at least 80% of the UV-B radiation in the range 310–320 nm but substantially all UV-B in the range 290–310 nm; said substrate containing at least one second agent which prevents transmittal of a biologically significant proportion, being 50% or more, of the visible and IR radiation of wavelengths in the range 450–700 nm and 700–15,000 nm respectively through said substrate, said agents being substantially uniformly dispersed throughout said substrate; and
 at least one third agent which is a heat absorbing material,
 wherein the relatively small portion of UV-B not absorbed by the apparatus stimulates the production of new melanin in a sunbather, which will be later available for tanning by UV-A radiation.

2. Apparatus according to claim 1 wherein said substrate comprises a sheet.

3. Apparatus according to claim 2, wherein said substrate comprises thermoplastic material.

4. Apparatus according to claim 3 wherein the thermoplastic material is a homopolymer of resin selected from the group consisting of styrene, butadiene, vinyl chloride, polyolefin, and an acrylic resin.

5. Apparatus according to claim 1 wherein said substrate is a synthetic fiber selected from the group consisting of nylon and polyester.

6. Apparatus according to claim 1 wherein said substrate comprises a thermoplastic material and the concentration ratio of the weight of said first agent to the weight of said thermoplastic material absent said first, second and third agents is between 0.01/100 and 0.5/100.

7. Apparatus according to claim 1, wherein the concentration ratio of the weight of said second agent to the weight of said substrate absent said first, second and third agents is less than 2.5/100.

8. Apparatus according to claim 1 wherein the second agent comprises a light and heat stable pigment.

9. Apparatus of claim 1, wherein the concentration ratio of the weight of said third agent to the weight of said substrate absent said first, second and third agents is less than 0.5/100.

10. Apparatus according to claim 1 wherein said substrate is supported by a framework.

11. Apparatus according to claim 1 wherein said substrate comprises a flexible plastic fiber fabricated into wearing apparel.

* * * * *